(12) United States Patent
Yeh et al.

(10) Patent No.: US 10,835,603 B2
(45) Date of Patent: Nov. 17, 2020

(54) METHOD FOR NORMALIZING BLOOD VESSELS OF LESIONS BY OXYGEN-LOADED MICROBUBBLES AND ULTRASONIC IRRADIATION

(71) Applicant: National Tsing Hua University, Hsinchu (TW)

(72) Inventors: Chih-Kuang Yeh, Hsinchu (TW); Yi-Ju Ho, Hsinchu (TW); Shu-Wei Chu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 42 days.

(21) Appl. No.: 16/198,085

(22) Filed: Nov. 21, 2018

(65) Prior Publication Data

US 2019/0365895 A1 Dec. 5, 2019

(30) Foreign Application Priority Data

Jun. 1, 2018 (TW) .............................. 107118920 A

(51) Int. Cl.
| | |
|---|---|
| *A61K 41/00* | (2020.01) |
| *A61K 9/00* | (2006.01) |
| *A61K 9/50* | (2006.01) |
| *A61P 9/00* | (2006.01) |
| *A61K 9/48* | (2006.01) |
| *A61K 33/00* | (2006.01) |
| *A61P 35/00* | (2006.01) |

(52) U.S. Cl.
CPC ........ *A61K 41/0028* (2013.01); *A61K 9/0019* (2013.01); *A61K 9/485* (2013.01); *A61K 9/4858* (2013.01); *A61K 9/5015* (2013.01); *A61K 33/00* (2013.01); *A61P 9/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 5,403,575 A | 4/1995 | Kaufman et al. | |
| 5,785,950 A | 7/1998 | Kaufman et al. | |
| 6,088,613 A | 7/2000 | Unger | |
| 6,649,145 B2 | 11/2003 | McGrath et al. | |
| 8,764,658 B2 | 7/2014 | Fawzi et al. | |
| 9,788,811 B2 | 10/2017 | Wu et al. | |
| 2003/0083610 A1 | 5/2003 | McGrath et al. | |
| 2004/0166171 A1 | 8/2004 | McGrath et al. | |
| 2007/0059248 A1 | 3/2007 | Unger et al. | |
| 2013/0289398 A1* | 10/2013 | Borden ................. | A61B 8/481 600/431 |
| 2014/0199261 A1 | 7/2014 | Nicolau et al. | |
| 2016/0059036 A1 | 3/2016 | Eisenbrey et al. | |

FOREIGN PATENT DOCUMENTS

| | | |
|---|---|---|
| CN | 1600294 A | 3/2005 |
| TW | 311091 B | 7/1997 |
| TW | I577343 B | 4/2007 |

OTHER PUBLICATIONS

Jianqun Han et al."Effect of artificial oxygen carrier with chemotherapy on tumor hypoxia and neovascularization" Artif Cells Blood Substit Immobil Biotechnol. 2008;36(5): pp. 431-438.

James J. Kwan et al. "Theranostic Oxygen Delivery Using Ultrasound and Microbubbles" Theranostics. 2012; 2(12); pp: 1174-1184.

* cited by examiner

*Primary Examiner* — Jessica Worsham

(74) *Attorney, Agent, or Firm* — Muncy, Geissler, Olds & Lowe, P.C.

(57) ABSTRACT

A method for normalizing blood vessels of lesions is disclosed, which includes administering an effective amount of oxygen-loaded microbubbles to a subject in need by intravenous injection, and projecting ultrasound from a ultrasonic emission device into the lesions for rupturing the oxygen-loaded microbubbles and releasing the oxygen to the lesions. Each of the oxygen-loaded microbubbles comprises oxygen and a water insoluble gas, and the particle size of microbubbles is 0.5~20 μm.

8 Claims, 4 Drawing Sheets

METHOD FOR NORMALIZING BLOOD VESSELS OF LESIONS BY OXYGEN-LOADED MICROBUBBLES AND ULTRASONIC IRRADIATION

CROSS REFERENCE TO RELATED APPLICATIONS

This application claims the benefits of the Taiwan Patent Application Serial Number 107118920, filed on Jun. 1, 2018, the subject matter of which is incorporated herein by reference.

FIELD OF THE INVENTION

The present invention relates to a method for normalizing blood vessels of lesions and, more particularly, to a method for normalizing blood vessels of lesions by intravenously injecting oxygen-loaded microbubbles and then projecting ultrasound into the lesions to induce local release of oxygen at the lesions.

DESCRIPTION OF RELATED ART

After the tumor tissue grows to a certain extent, it must rely on the neovascularization to supply its nutrients. Therefore, the tumor cells themselves or the surrounding connective tissue secrete many growth factors for promoting neovascularization to induce the formation of new blood vessels at the tumor to supply the tumor cells with nutrients. However, the newly-formed vessels inside the tumor are abnormally proliferated, resulting in tortuosity and non-uniform diameter of blood vessels, numerous pores on the blood vessel wall, and reduced function of blood vessels for transporting blood. Even if the drug is administered to the tumor tissue, the administered drug cannot reach the inside of the tumor tissue smoothly, so the treatment effect is limited.

In order to enhance the efficiency of tumor therapy, the drugs for normalizing tumor blood vessels are usually administered before dosing therapy. However, the conventional drugs usually have a short expiration date, so the time during which the therapeutic drug actually reaches the inside of the tumor is limited, and the therapeutic effects on tumors are often limited.

Normalization of tumor blood vessels is helpful in the delivery of therapeutic drugs. Therefore, there is a need for normalizing blood vessels of tumor tissue, improving the vascular morphology and function of tumor tissue, and further prolonging the time window of blood vessel normalization.

SUMMARY OF THE INVENTION

To achieve the above objective, the present invention provides a method for normalizing blood vessels of lesions, including: administering an effective amount of oxygen-loaded microbubbles to a subject in need by intravenous injection, wherein each of the oxygen-loaded microbubbles comprises oxygen and water insoluble gas, and has a particle size in a range of 0.5 to 20 μm; and projecting ultrasound from a ultrasonic emission device into the lesions for rupturing the oxygen-loaded microbubbles and releasing the oxygen to the lesions.

In one embodiment of the present invention, the particle size of the oxygen-loaded microbubbles is preferably in a range of 0.7 to 3.0 μm, wherein the number of the oxygen-loaded microbubbles having the particle size of larger than 3.0 μm is 0.5 percent based on the total number of the oxygen-loaded microbubbles.

In one embodiment of the present invention, the volume ratio of the water insoluble gas to the oxygen in the oxygen-loaded microbubbles is in a range of 1:1 to 3:1, and preferably in a range of 1:1 to 1.4:1.

In one embodiment of the present invention, the water insoluble gas contained in the oxygen-loaded microbubbles is at least one selected from the group consisting of perfluoropropane ($C_3F_8$), perflubutane ($C_4F_{10}$), nitrogen ($N_2$), carbon dioxide ($CO_2$), and the mixtures thereof, and preferably is perfluoropropane.

In one embodiment of the present invention, the oxygen-loaded microbubbles further comprise a phospholipid shell covering the oxygen and the water insoluble gas. Preferably, the phospholipid shell consists of 1,2-distearoyl-sn-glycero-3-phosphorylcholine and 1,2-distearoyl-sn-glycero-3-phosphoethanolamine-N-[10-(trimethoxysilyl) undecanamide (polyethyleneglycol)-2000].

In one embodiment of the present invention, the effective dose of oxygen-loaded microbubbles ranges from 2.5 to 3.5 μL/kg per day.

In one embodiment of the present invention, the ultrasonic emission device is a high intensity focused ultrasonic emission device.

In one embodiment of the present invention, the ultrasonic emission device is set to parameters of 2 MHz in sound frequency, 1.5 to 2.5 MPa in sound pressure, 500 to 1500 in period, and 1 to 5 Hz in pulse repetition frequency.

In one embodiment of the present invention, the lesions are tumor tissues, thrombosis-induced hypoxic normal tissues or injured blood vessels.

DETAILED DESCRIPTION OF THE PREFERRED EMBODIMENTS

Preparation of Oxygen-Loaded Microbubbles by Thin-Film Hydration

In this embodiment, oxygen-loaded microbubbles were produced by thin-film hydration, which includes the following steps: (1) preparation of phospholipid thin film: (1,2-Distearoyl-sn-glycero-3-phosphorylcholine; DSPC) of 2.5 mg and the (1,2-distearoyl-sn-glycero-3-phosphoethanolamine-N-[10-(trimethoxysilyl)undecanamide (poly ethyleneglycol)-2000]; DSPE-PEG-2000) of 1 mg were added to a 2 ml sample bottle, and uniformly dissolved in 0.25 mL chloroform solvent, and the chloroform was drained by heating at 60° C. for 1 hour by water bath method; subsequently, the organic solvent was completely removed under vacuum for 24 hours using rotary evaporation to form a lipid thin film on the bottom of the sample bottle, followed by storing the sample bottle at −20° C.; and (2) preparation of oxygen-loaded microbubbles: the phosphate buffered saline (PBS) was mixed with glycerin by a volume ratio of 20:0.1, then the 0.8 ml PBS-glycerin mixture was added to the sample bottle, followed by water-bath heating at 60° C. for 10 minutes and then using a water bath type ultrasonic homogenizer (Model 2510, Branson, N.Y., USA) to dissolve and mix uniformly the phospholipid membrane; subsequently, the sample bottle was evacuated by a suction pump and then filled with perfluoropropane ($C_3F_8$) gas, followed by removal of the perfluoropropane gas and then introduction of oxygen into the sample bottle; and finally, the oxygen-loaded microbubbles were formed through the self-assembly of the phospholipid molecules to encapsulate perfluoropropane and oxygen by oscillation for 45 seconds at room temperature using a high-speed oscillator (VIALMIX, Bristol-Myers Squibb Medical Imaging, NY, USA). In this embodiment, the volume ratio of perfluoropropane:oxygen in the sample bottle was adjusted to be 1:1, 1.4:1, 2:1, 3:1, 1:0, and the optimum gas volume ratio of perfluoropropane:oxygen in the sample bottle was determined by the particle size distribution and concentration of the oxygen-loaded microbubbles.

Particle Size Distribution and Concentration of Oxygen-Loaded Microbubbles

Figure 1:
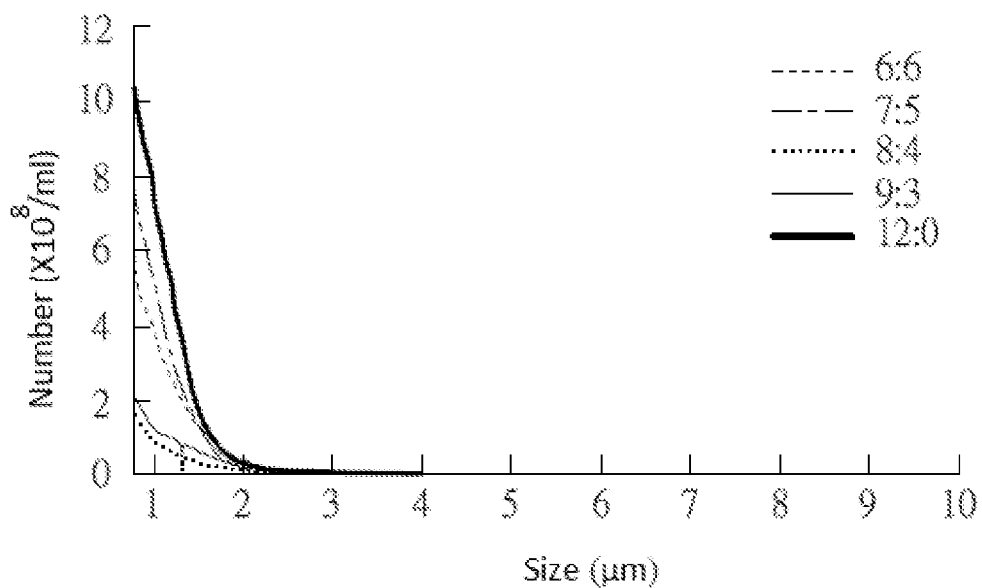
FIG. 1 shows the particle size distribution of oxygen-loaded microbubbles in different volume ratios of perfluoropropane to oxygen.
Figure 2:
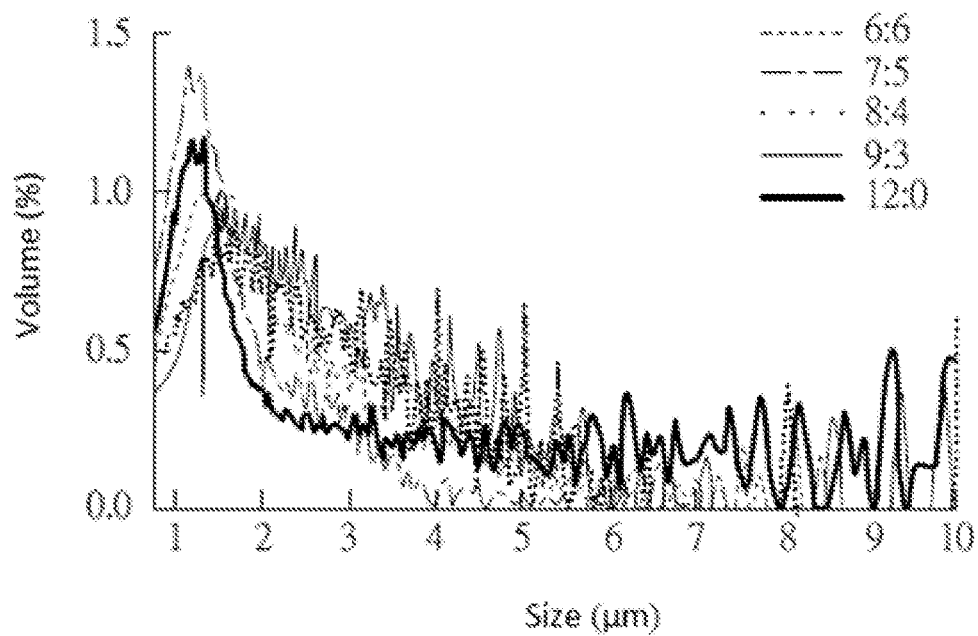
FIG. 2 shows the volume distribution of oxygen-loaded microbubbles in different volume ratios of perfluoropropane to oxygen.

The particle size distribution, concentration, average particle size, and volume distribution of the above-mentioned oxygen-loaded microbubbles (volume ratio of perfluoropropane/oxygen being 1:1, 1.4:1, 2:1 and 3:1, respectively) and the perfluoropropane microbubbles in the comparison group (volume ratio of perfluoropropane/oxygen being 1:0) were measured using a particle size analyzer. The average particle size and concentration are shown in table 1, and the particle size and volume distribution are shown in FIGS. 1 and 2, respectively.

TABLE 1

Average particle size and concentration of oxygen-loaded microbubbles in different gas ratios.

| $C_3F_8:O_2$ | Average particle size (μm) | Concentration ($\times 10^{10}$ oxygen-loaded microbubbles/mL) |
|---|---|---|
| 1:1 | 3.11 ± 1.40 | 1.10 ± 0.47 |
| 1.4:1 | 1.02 ± 0.03 | 2.04 ± 0.36 |
| 2:1 | 2.45 ± 0.82 | 0.54 ± 0.05 |
| 3:1 | 2.80 ± 0.47 | 1.03 ± 0.04 |
| 1:0 | 0.99 ± 0.02 | 4.14 ± 0.22 |

FIGS. 1 and 2 show that the oxygen-loaded microbubbles in perfluoropropane/oxygen volume ratios of 1:1 and 3:1 have more microbubbles larger than 2 μm and lower total concentration. As for the oxygen-loaded microbubbles produced in perfluoropropane/oxygen volume ratio of 1.4:1, their particle size and volume distribution were similar to those of the perfluoropropane microbubbles in perfluoropropane/oxygen volume ratio of 1:0 (please referring to Table 1). Therefore, the following measurements and in vivo experiments were conducted using the oxygen-loaded microbubbles prepared in the perfluoropropane/oxygen volume ratio of 1.4:1.

Amount of Dissolved Oxygen in Oxygen-Loaded Microbubbles

There were five groups, degassed PBS, PBS+ perfluoropropane+ oxygen, perfluoropropane microbubbles, oxygen-loaded microbubbles ($C_3F_8:O_2=1.4:1$) and washed oxygen-loaded microbubbles ($C_3F_8:O_2=1.4:1$), to be measured for dissolved oxygen using a dissolved oxygen meter.

Figure 3:
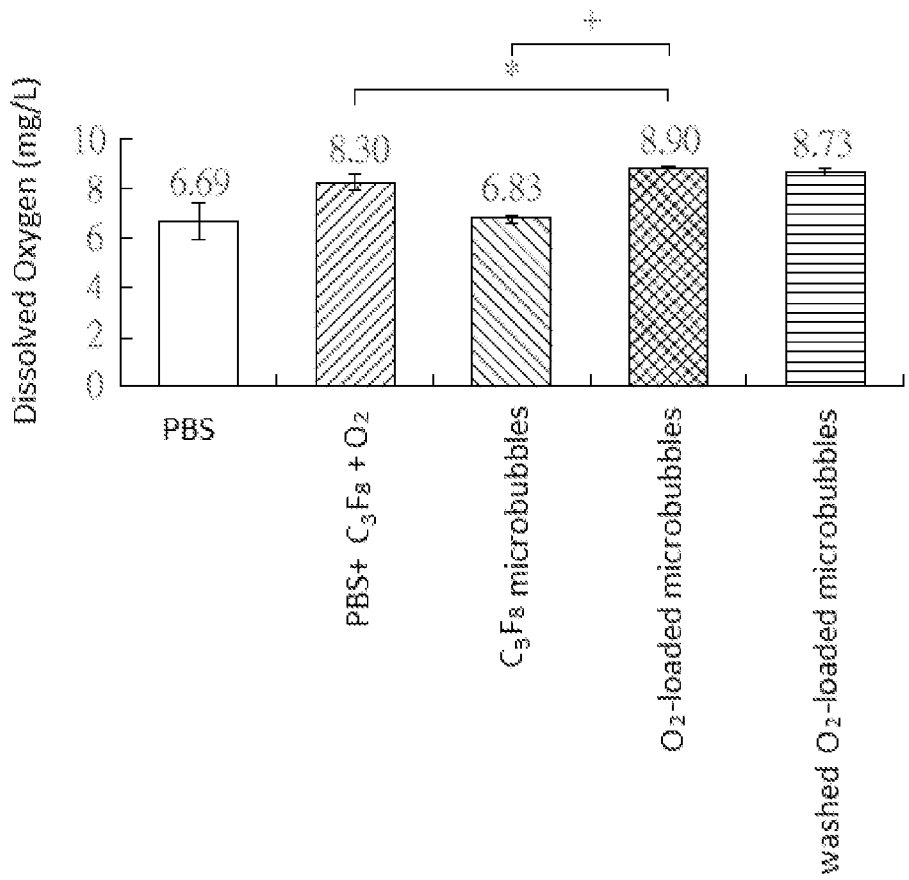
FIG. 3 shows the change in dissolved oxygen content of microbubbles in different groups.

The PBS+ perfluoropropane+ oxygen refers to an aerated aqueous solution without gas-encapsulated microbubbles. The washed oxygen-loaded microbubbles refer to the oxygen-loaded microbubbles obtained by replacing the subnatant with the degassed PBS after centrifugation at 2000 rcf for one minute. For the washed oxygen-loaded microbubbles, the dissolved oxygen in the PBS solution was eliminated so as to calculate the oxygen concentration in the oxygen-loaded microbubbles. The dissolved oxygen amount was measured by placing 800 μL of the fully dissolved oxygen-loaded microbubbles in a 20 mL sample vial, and inserting the dissolved oxygen meter probe into it to submerge the monitor at the top of the probe in the oxygen-loaded microbubbles. During the measurement, the probe of the dissolved oxygen meter should be fixed by a three-axis platform. The measured values of dissolved oxygen of all groups were recorded when being indicated as "value stable". As shown in FIG. 3 regarding the dissolved oxygen variations of all the above groups, the amount of dissolved oxygen of the oxygen-loaded microbubbles prepared in perfluoropropane/oxygen volume ratio of 1.4:1 was 8.9±0.02 mg/L, which increased by 2.07±0.14 mg/L compared to the perfluoropropane microbubbles. Comparing the oxygen-loaded microbubbles with the washed oxygen-loaded microbubbles regarding dissolved oxygen, it can be found that the PBS-replacement does not cause significant change in dissolved oxygen ($p>0.05$). From the measurement results, it is known that oxygen is mostly encapsulated in microbubbles and is not dissolved in PBS.

Stability of Oxygen-Loaded Microbubbles

In this embodiment, a commercial ultrasonic imaging system (Model 3000, Terason, Burlington, Mass.) was used with a self-made phantom for simulation of the acoustic stability of oxygen-loaded microbubbles and perfluoropropane microbubbles in a living body at 37° C.

The phantom was constructed using agar powder (Ultra-Pure™ Agarose, Invitrogen, CA, USA). The agar powder with a weight percentage of 2% was uniformly mixed with the distilled deionized water (DDW), and completely dissolved during heating and stirring. When the mixed solution become clear and transparent, it was poured into a self-made phantom container for styling. Before solidification, a 0.5 cm solid cylindrical glass tube model was inserted therein to form a phantom cavity. After the phantom was fully cured, the glass tube model was removed and the preparation of the phantom can be completed.

Then, the phantom was first submerged in the degassed water, and the image probe of the ultrasonic imaging system was clamped by a jig. The oxygen-loaded microbubbles ($C_3F_8:O_2$=1.4:1) and perfluoropropane microbubbles diluted 4000 times with physiological saline were respectively injected into the phantom cavity, followed by imaging. In order to simulate the living environment of the living body, a heating rod was used to control the temperature of the water tank at 37° C. The ultrasonic images were taken with one image every 10 minutes over a 60-min period.

Figure 4:
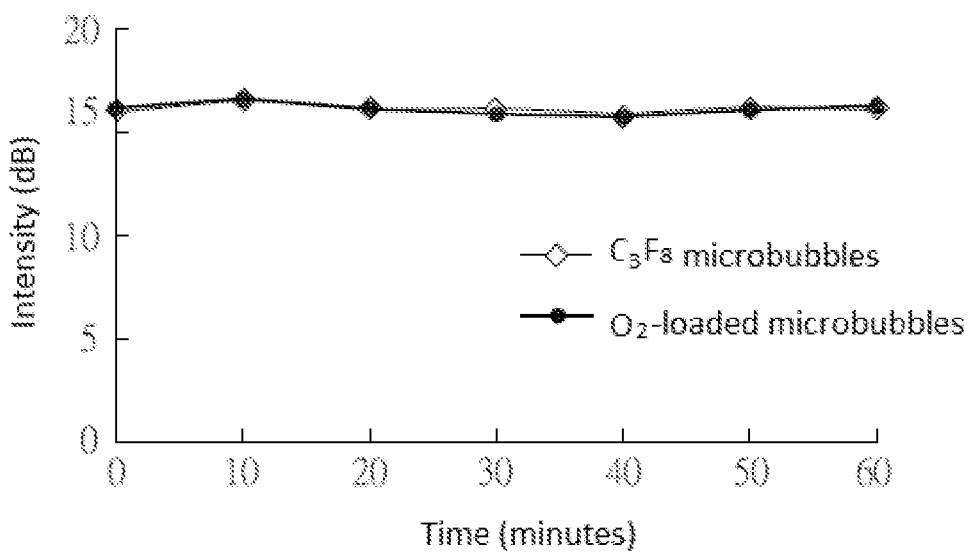
FIG. 4 shows the brightness variation of ultrasound images of perfluoropropane microbubbles and oxygen-loaded microbubbles.

After repeating three times of experiments, image analysis was performed using MATLAB (2010a; MathWorks, Natick, Mass., USA) to quantify the image contrast effects of oxygen-loaded microbubbles and perfluoropropane microbubbles. Regions of interest (ROI) of the same size were drawn at every time points, and signal-to-noise ratio (SNR) was estimated by dividing the signal in the ROI with the background intensity of water at the same height, thereby obtaining the change of the acoustic intensity signal at different time points. As shown in FIG. 4, no significant decrease in image brightness was observed within 60 minutes for the oxygen-loaded microbubbles and the perfluoropropane microbubbles under the ultrasound imaging system. It was confirmed that the addition of oxygen to the microbubbles would not render the microbubbles unstable.

In Vivo Experiments for Evaluation of Promoting Effect of Oxygen-Loaded Microbubbles on Normalization of Blood Vessels In this embodiment, male C57BL/6JNarl mouse strains (age, 6-8 weeks; weight, 30 g) were obtained from the National Animal Experimental Center. For in vivo subcutaneous tumor model test, $1\times10^6$ TRAMP (Transgenic Adenocarcinoma Mouse Prostate cell line) cells were implanted into the right leg of the mouse. When the tumor grew to a diameter of about 7 mm after 7 days, the mice were anesthetized with 50 μL of a mixture of Zoletil (Zoletil 50, Virbac, TW) and Rompun (Rompun 20, Bayer, TW) in a volume ratio of 1:1 by intraperitoneal injection. After the mice were anesthetized, the hair of the tumor position was shaved with a razor, and the hair removal cream was evenly applied to completely clean the epidermal area of the tumor. During the experiment, the body temperature of the mice was maintained at 37° C. with a heating pad to avoid the temperature loss.

Then, the ultrasound image guided therapy system was set up for live verification. The right hind leg of the tumor-bearing mouse was placed under the self-made water tank containing the plastic wrap window, and the probe of the 2 MHz high-intensity focused ultrasound (HIFU) and the image sensor of the commercial ultrasound imaging system were placed in the water tank to focus on the same slice of the subcutaneous tumor. The 2 MHz high-intensity focused ultrasound probe was used to burst the oxygen-loaded microbubbles, resulting in release of oxygen. At the same time, the treatment process can be monitored by the ultrasound image provided by the image sensor of the commercial ultrasound imaging system so as to locate the tumor position and adjust the treatment area.

The detailed experimental process is described as follows:

(1) Blood perfusion imaging of whole tumor before oxygen supply: First, the perfluoropropane microbubbles were intravenously injected into mice to obtain information on blood perfusion. In order to acquire an ultrasound image of the whole tumor, the tumor contained a constant concentration of perfluoropropane microbubbles. In this embodiment, the perfluoropropane microbubbles in a concentration of $2\times10^9$/mL were continuously injected into the eye orbit of the mouse through an infusion pump at an injection velocity of 0.3 mL/h. After circulating the perfluoropropane microbubbles for 1 minute, the mice were imaged using a commercial ultrasound imaging system, with a three-axis platform for moving mice, to acquire cross-sectional images at intervals of 0.5 mm so as to obtain the blood perfusion image of the whole tumor before oxygen supply.

(2) Release of oxygen from oxygen-loaded microbubbles: After waiting for 30 minutes to complete the metabolism of the perfluoropropane microbubbles, the first dose of $1\times10^7$ oxygen-loaded microbubbles ($C_3F_8:O_2$=1.4:1; N=9) was injected into the eye orbit, and after 1 minute of circulation, the oxygen-loaded microbubbles were burst to release oxygen using the high-intensity focused ultrasonic probe at a sound pressure of 2 MPa, a period of 1000, and a pulse repetition frequency (PRF) of 2 Hz. After 6 seconds of ultrasonic irradiation, the irradiation was stopped for 6 seconds to ensure that oxygen-loaded microbubbles were supplied into the blood vessels before next ultrasonic irradiation, and the mouse was moved with a three-axis platform. After half of the tumor was treated (about 10 minutes after the injection), a second dose of $1\times10^7$ oxygen-loaded microbubbles was injected, followed by scanning the other half of the tumor with high-intensity focused ultrasound. The scan time was about 20 minutes in total. By two doses of $1\times10^7$ oxygen-loaded microbubbles, the oxygen-loaded microbubbles in the anterior and posterior segments of the tumor can be uniformly scanned by the high-intensity focused ultrasound. In this experiment, the total therapeutic dose of $2\times10^7$ oxygen-loaded microbubbles per mouse is within the safe dose range of $3.9\times10^7$ to $6.9\times10^7$ microbubbles/mouse. In addition, a control group without injection and ultrasonic irradiation (N=6) and a comparison group with injection of perfluoropropane microbubbles and ultrasonic irradiation (N=8) were also given in this experiment. Unlike the injection of oxygen-loaded microbubbles in the experimental group, the experiment for the comparison group was carried out by injecting perfluoropropane microbubbles.

(3) Blood perfusion image of the whole tumor after oxygen administration: The time points for acquiring the blood perfusion images of whole tumor were day 0 (after 1 minute), 2, 4, 6, and 8 after injection of oxygen-loaded microbubbles (experimental group) or injection of perfluoropropane microbubbles (comparison group). The method of acquiring the images was the same as the above step (1): the perfluoropropane microbubbles in a concentration of $2\times10^9$/mL were continuously injected into the eye orbit of the mouse through an infusion pump at an injection velocity of 0.3 mL/h; and after circulating the perfluoropropane microbubbles for 1 minute, the mice were imaged using a commercial ultrasound imaging system, with a three-axis platform for moving mice, to acquire sliced images at intervals of 0.5 mm so as to obtain the blood perfusion image of the whole tumor after oxygen supply. The ultrasound images were then further analyzed to calculate the blood perfusion ratio as shown in FIG. 5 and the density of the tumor vessels as shown in FIG. 6, and to ascertain whether function restoration associated with vascular normalization or angiogenesis caused the change in tumor blood perfusion.

Figure 5:
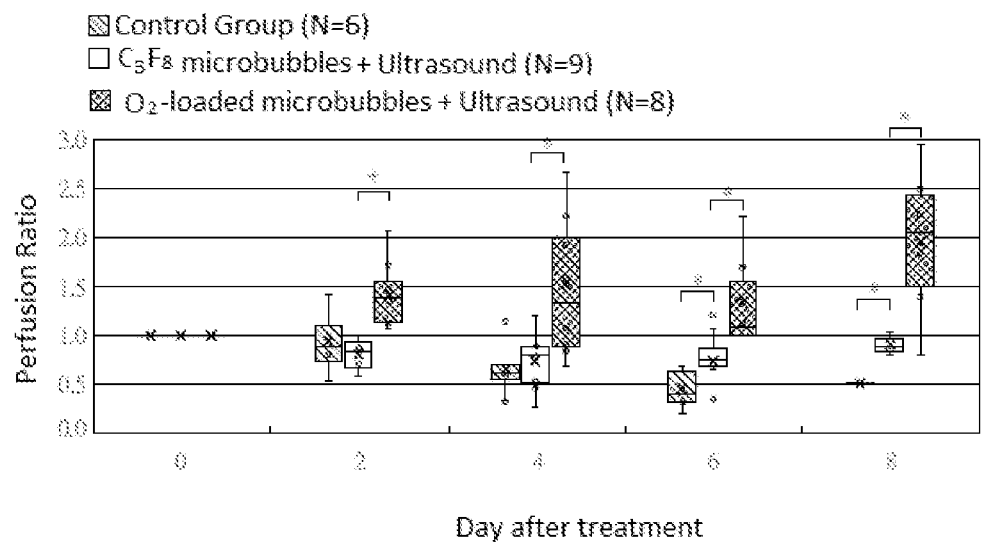
FIG. 5 shows the perfusion ratio after ultrasound mediated local release of oxygen from perfluoropropane microbubbles and oxygen-loaded microbubbles into the tumor.
Figure 6:
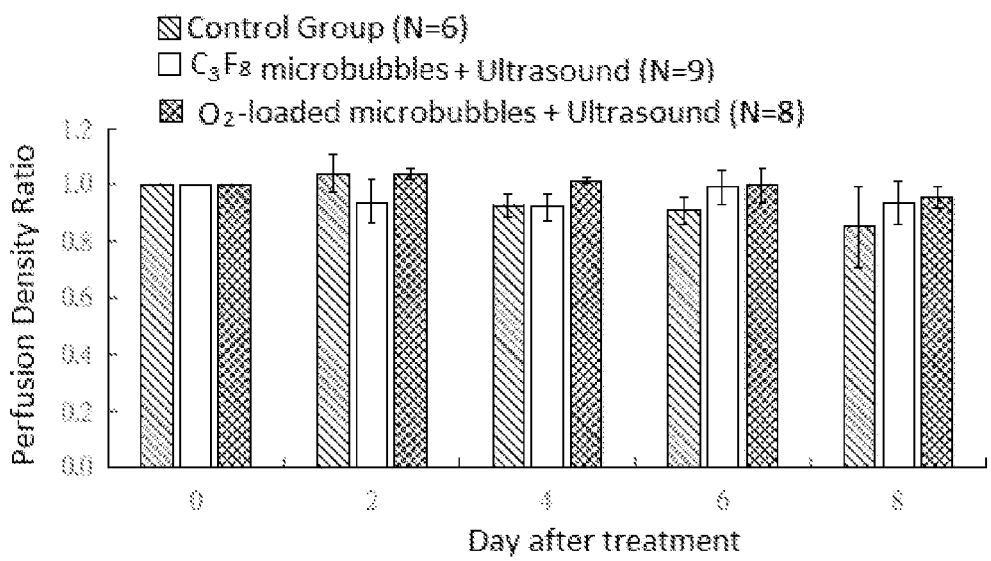
FIG. 6 shows the tumor vessel density after ultrasound mediated local release of oxygen from perfluoropropane microbubbles and oxygen-loaded microbubbles into the tumor.

The experimental results shown in FIG. 5 indicated that the blood perfusion ratio significantly increased only in the experimental group with the injection of oxygen-loaded microbubbles and ultrasonic irradiation. Even the blood perfusion ratio on the 8th day after oxygen administration was maintained at 1.95±0.78 in the experimental group. On the contrary, the control group and the comparison group with injection of the perfluoropropane microbubbles and ultrasonic irradiation showed lower blood perfusion ratio (<1) on the $2^{nd}$ to $4^{th}$ day. Therefore, it is proved that the blood vessels of the tumor can be normalized through delivery of oxygen-loaded microbubbles and ultrasound mediated local release of oxygen, resulting in the increase of tumor blood perfusion. Furthermore, from the experimental results shown in FIG. 6, it can be seen that no significant increase or decrease in the density of tumor blood vessels was observed in the experimental group (N=5), the comparison group (N=4), and the control group (N=6). Therefore, it can be inferred that the increase in tumor blood perfusion ratio is due to the normalization of vascular function rather than neovascularization.

Figure 7:
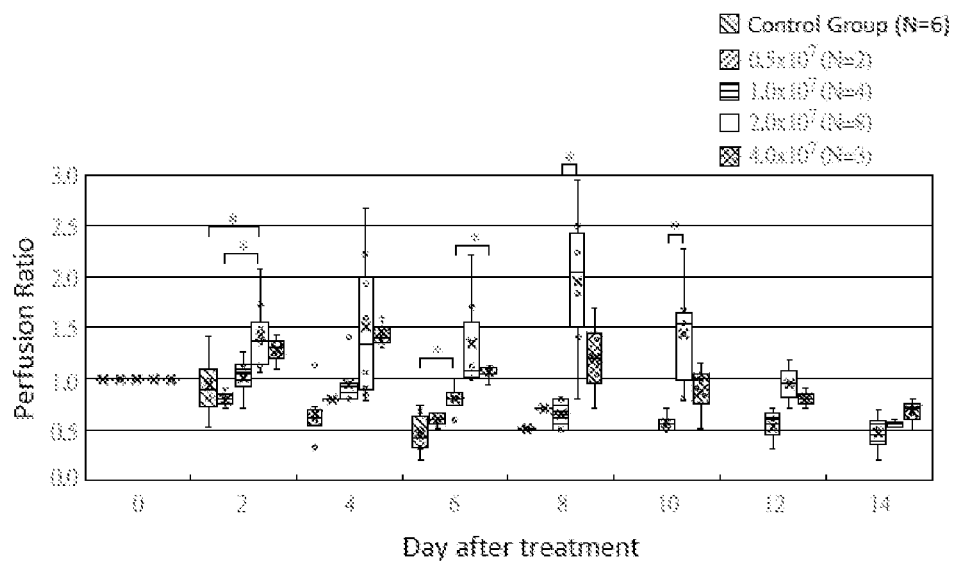
FIG. 7 shows tumor blood perfusion ratio of the tumor at different doses of oxygen-loaded microbubbles.

In Vivo Experiments for Evaluation of Time Window Length for Oxygen-Loaded Microbubbles to Promote Normalization of Blood Vessels This experiment was conducted by the same procedure as mentioned in the above experimental group, except that different oxygen-loaded microbubble doses of $0.5 \times 10^7$ (N=2), $1 \times 10^7$ (N=4), $2 \times 10^7$ (N=8), $4 \times 10^7$ (N=3) per mouse were administered in different groups. In addition, a control group without injection and ultrasonic irradiation (N=6) was also given in this experiment. FIG. 7 shows the changes in tumor blood perfusion ratio at different doses. From the results shown in FIG. 7, it can be known that the dose of oxygen-loaded microbubbles would affect the length of time window for normalization of blood vessels. Compared to the control group, the group with the dose of $2 \times 10^7$ oxygen-loaded microbubbles per mouse presented significant increase of blood perfusion ratio from the second day. On the basis of the perfusion ratio of 1, the time window for normalization of blood vessels was determined as $2^{nd}$ day to $10^{th}$ day after oxygen administration.

Analysis of Factors Related to Vascular Normalization

In this embodiment, the fourth day after oxygen administration was determined as the time point for normalization of blood vessels, and the mice were sacrificed on the fourth day after oxygen administration. The whole tumor was taken for tissue extraction, and expressions of prolyl hydroxylase domain-containing protein 2 (PHD2), hypoxia-inducible factor-1α (HIF-1α), vascular endothelial growth factor (VEGF), and transforming growth factor-β (TGF-β) were measured by western blot. The measurement results are shown in FIG. 8.

According to the literature, normalization of tumor blood vessels can increase the efficiency of oxygen delivery. In a high oxygen concentration environment, the oxygen-detecting enzyme (PHD2) in vascular endothelial cells decomposes hypoxia-inducible factor (HIF-1a), resulting in reduced expression of HIF-1α, decreased expression of the vascular endothelial growth factor (VEGF) in downstream genes, and slowed growth rate of tumor blood vessels. Therefore, there is sufficient time to repair abnormal blood vessels in the tumor, so that tumor blood vessels are normalized. In addition, the amount of expression of transforming growth factor (TGF-β) can be used to assess whether the rate of tumor cell proliferation is affected after tumor vascular normalization.

Figure 8:
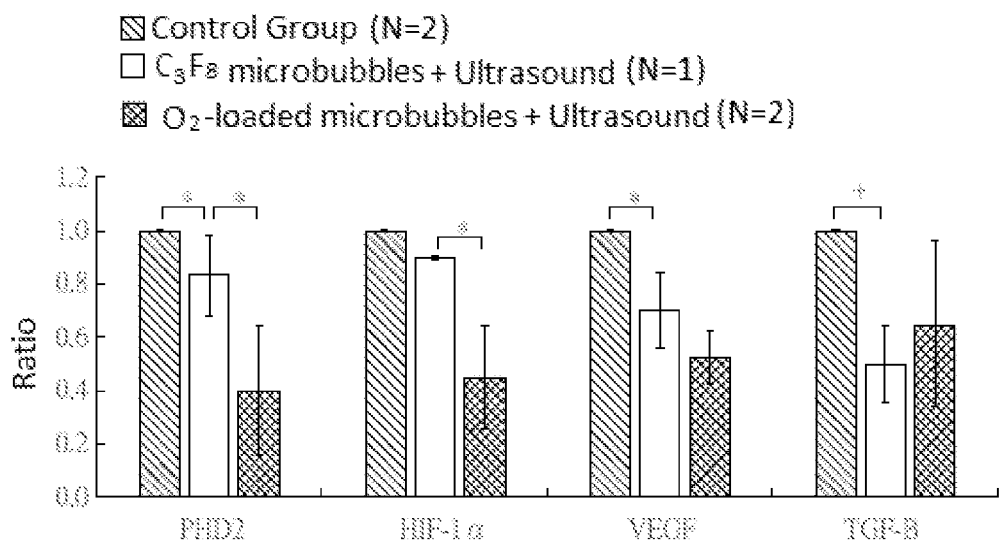
FIG. 8 shows the expression levels of PHD2, HIF-1α, VEGF, and TGF-0 on the fourth day after administration of perfluoropropane microbubbles and oxygen-loaded microbubbles.

As shown in FIG. 8, the expressions of PHD2, HIF-1α, and VEGF were decreased after normalization of blood vessels by the injection of oxygen-loaded microbubbles and ultrasound mediated release of oxygen at the tumor site, and no significant difference was observed in TGF-β. As the decrease in the expression levels of PHD2, HIF-1α, and VEGF is consistent with the above theory, it is further confirmed that the release of oxygen at the tumor site by the oxygen-loaded microbubbles can induce normalization of tumor blood vessels.

Statistical Analysis

The data were statistically analyzed using the Student's t-test two-tailed test.

Based on the above test results, it is confirmed that the injection of oxygen-loaded microbubbles followed by ultrasound mediated release of oxygen at the tumor site can induce normalization of blood vessels at the tumor site, thereby increasing blood perfusion at the tumor site and prolonging the time window of normalization of the blood vessel to be $2^{nd}$ day to $10^{th}$ day after oxygen supply.

What is claimed is:

1. A method for normalizing blood vessels of lesions, comprising:
    administering an effective amount of oxygen-loaded microbubbles to a subject in need by intravenous injection, wherein each of the oxygen-loaded microbubbles includes oxygen and water insoluble gas, and has a particle size in a range of 0.5 to 20 μm; and
    projecting ultrasound from a ultrasonic emission device into the lesions for rupturing the oxygen-loaded microbubbles and releasing the oxygen to the lesions;
    wherein each of the oxygen-loaded microbubbles includes the water insoluble gas and the oxygen in a volume ratio of 1.4:1; wherein the ultrasonic emission device is high intensity focused ultrasonic emission device and is set to parameters of 1.5 to 2.5 MPa in sound pressure.

2. The method of claim 1, wherein the particle size of the oxygen-loaded microbubbles is in a range of 0.7 to 3.0 μm.

3. The method of claim 1, wherein the water insoluble gas included in the oxygen-loaded microbubble is at least one selected from the group consisting of perfluoropropane ($C_3F_8$), perflubutane ($C_4F_{10}$), nitrogen ($N_2$), carbon dioxide ($CO_2$) and a mixture thereof.

4. The method of claim 1, wherein each of the oxygen-loaded microbubbles further includes a phospholipid shell encapsulating the oxygen and the water insoluble gas.

5. The method of claim 4, wherein the phospholipid shell consists of 1,2-di stearoyl-sn-glycero-3-phosphorylcholine and 1,2-di stearoyl-sn-glycero-3-phosphoethanolamine-N-[10-(trimethoxysilyl) undecanamide (polyethyleneglycol)-2000].

6. The method of claim 1, wherein the oxygen-loaded microbubbles are administered at a daily dosage of 2.5 to 3.5 μL per kilogram of a body weight of the subject.

7. The method of claim 1, wherein the ultrasonic emission device is set to parameters of 500 to 1500 in period, and 1 to 5 Hz in pulse repetition frequency.

8. The method of claim 1, wherein the lesions are tumor tissues, thrombosis-induced hypoxic tissues or injured blood vessels.

* * * * *